United States Patent [19]

Fedorov et al.

[11] Patent Number: 6,165,490
[45] Date of Patent: Dec. 26, 2000

[54] BIOLOGICAL MATERIAL, METHOD OF PREPARING SUCH MATERIALS, USES THEREOF AND PRODUCTS MADE THEREFROM

[75] Inventors: Svyatoslav Nikolayevich Fedorov; Sergei Nikolayevich Bagrov; Yevgeny Viktorovich Larionov, all of Moscow, Russian Federation

[73] Assignee: STAAR Surgical AG, Nidau, Switzerland

[21] Appl. No.: 08/931,448

[22] Filed: Sep. 16, 1997

Related U.S. Application Data

[63] Continuation-in-part of application No. 08/628,379, Apr. 5, 1996, abandoned.

[51] Int. Cl.$^7$ .................................................. A61K 35/34
[52] U.S. Cl. ......................... 424/427; 424/400; 424/569
[58] Field of Search .................................. 424/422, 400, 424/569, 427

[56] References Cited

U.S. PATENT DOCUMENTS

| | | | |
|---|---|---|---|
| Re. 33,997 | 7/1992 | Kuzma et al. | 523/106 |
| 4,042,457 | 8/1977 | Kuettner et al. | 195/1.8 |
| 4,064,008 | 12/1977 | Petersen et al. | 195/6 |
| 4,220,724 | 9/1980 | Berg et al. | 435/273 |
| 4,861,760 | 8/1989 | Mazuel et al. | 514/54 |
| 4,876,332 | 10/1989 | Tsilibary et al. | 530/326 |
| 4,894,441 | 1/1990 | Menicagli | 530/356 |
| 4,906,613 | 3/1990 | Watkins | 514/16 |
| 5,103,840 | 4/1992 | Kavoussi | 128/899 |
| 5,106,876 | 4/1992 | Kawamura | 522/5 |
| 5,210,182 | 5/1993 | Nasrallah et al. | 530/355 |
| 5,424,408 | 6/1995 | Reeders et al. | 536/23 |
| 5,476,515 | 12/1995 | Kelman et al. | 623/6 |

*Primary Examiner*—Thurman K. Page
*Assistant Examiner*—W. Benston
*Attorney, Agent, or Firm*—Law Offices of William L. Klima, P.L.C.

[57] ABSTRACT

A biological material is prepared for use in ophthalmology by steps of providing animal pericardium, subjecting the animal pericardium to multiple steps of freezing and thawing in a salt solution and incubating the animal pericardium in a solution of ammonia and ethyl alcohol. The multiple steps of freezing and thawing are conducted in a mixture of about 0.9% sodium chloride solution and distilled water in about 1:1 proportions of sodium chloride solution to distilled water. The incubating step is conducted in a mixture of 1% ammonia solution and 1% ethyl alcohol solution in about 1:1 proportions of ammonia solution to ethyl alcohol solution over a period of 48 to 72 hours.

22 Claims, No Drawings

BIOLOGICAL MATERIAL, METHOD OF PREPARING SUCH MATERIALS, USES THEREOF AND PRODUCTS MADE THEREFROM

RELATED APPLICATIONS

This application is a continuation-in-part application of U.S. Ser. No. 08/628,379, filed Apr. 5, 1996 now abandoned.

FIELD OF THE INVENTION

The invention relates to biological materials, methods of preparing such biological materials and uses thereof for example in ophthalmology. The invention may be used to produce anti-glaucoma drainage tubes for the surgical treatment of glaucoma, to produce collagen solutions to treat mild myopia and to produce pharmaceuticals for external use.

BACKGROUND OF THE INVENTION

Biological materials have been extracted from raw material of animal origin, such as pig eye sclera, by treatment with alkali and acetic acid solutions as shown in Soviet Inventor's Certificate No. 1747075, Cl. A 61 K 37/12. The material synthesized by this prior art method can be used in ophthalmological applications only after very lengthy and complex treatment. The material is characterized by extremely high solubility and low enzyme resistance. Hence, the material is not suitable for use in ophthalmology.

SUMMARY OF THE INVENTION

The present invention relates to biological materials and to the preparation of a biological materials for use in ophthalmology. In the invention, animal pericardium is provided and subjected to multiple steps of freezing and thawing in a salt solution. The pericardium is then incubated in a solution of ammonia and ethyl alcohol.

The present invention provides a method for the preparation of a biological material suitable for use in, for example ophthalmology.

It is an object of the invention to provide a method for the preparation of a material that is characterized by low solubility and high enzyme resistance.

Still another object of the invention is to provide a method to prepare a biological material from animal pericardium.

DETAILED DESCRIPTION OF THE INVENTION

Pericardium is the connective tissue of the heart. The pericardium contains very few vessels or cells and its stroma consists primarily of collagen, which is relatively insoluble, and is relatively non-immunogenic. Moreover, a solution of collagen made from the pericardium is highly enzyme resistant. Enzyme resistance is extremely important for making collagen polymer products for use invivo. The high enzyme resistance of the present material prevents the formation of scar tissue invivo, for example when the present material, in the form of a glaucoma drainage tube, no scar tissue forms at the site of insertion of the tube into the eye. The method of the present invention provides a versatile biological material, which can be used extensively to produce a number of products such as scleroplastic materials, anti-glaucoma drainage tubes, materials for treating macular dystrophies and materials for synthesizing liquid medications In the method of the present invention, animal pericardium is first mechanically cleaned. The cleaning removes fat, vessels and other contaminants. The cleaned pericardium is cut into pieces of desired size and configuration and the pieces are rinsed in tap water. The animal pericardium pieces are then subjected to multiple steps of freezing and thawing in a salt solution. The salt solution is preferably a mixture of about 0.9% sodium chloride solution and distilled water in about 1:1 proportions of sodium chloride solution to distilled water. The multiple steps of freezing and thawing extract high molecular weight proteins and glycoproteins. The high molecular weight proteins and glycoproteins are the primary immunogenic components in pericardium tissue. It has been found that about 3 to 7 repeated steps, preferably about 4 to 6 and most preferably about 5 repeated steps of freezing and thawing are sufficient to remove all proteins and glycoproteins.

After the multiple steps of freezing and thawing, the animal pericardium pieces are incubated in a mixture of 1% ammonia solution and 1% ethyl alcohol solution in about 1:1 proportions of ammonia solution to ethyl alcohol solution. The solution is prepared and is poured over the pieces. The pieces in solution are incubated for a period of from about 36 to 68 hours, preferably from about 48 to 72 hours, the solution is then drained and replaced with fresh solution and the tissue is again incubated for from about 36 to 68 hours, preferably from about 48 to 72 hours. The incubation steps remove lipoprotein and lipids from the pericardium tissue. The pericardium should be incubated for at least 48 hours to remove the lipids. Incubation for more than 72 hours can break down the pericardium collagen.

After incubation, the animal pericardium is subjected to multiple rinsing steps. The rinsing steps comprise rinsing the pericardium for about 3 to 7 times, preferably for about 5 times, for a time period of from about 10 to 35 minutes, preferably for from about 15 to 30 minutes, each time in distilled water. During the rinsing, the pH of the waste rinse water is periodically determined and a Vidal ammonia test is conducted to determine when rinsing (complete removal of ammonial and alcohol) is complete. It has been found that the ammonia/alcohol solution is removed after rinsing five times for a time period of at least 15 minutes for each rinse. Shorter rinse times leave traces of ammonia and leave acidic pH levels. All ammonia is removed by using a rinse time period of 30 minutes.

After rinsing, the pericardium is sterilized in a solution of about 70% ethyl alcohol and is then irradiated with about 2.5 megarads of gamma irradiation. Specifically, the rinsed pieces are packed in vials containing the alcohol and are sterilized by irradiating the vials.

The following examples are intended to illustrate the invention without limiting its scope.

EXAMPLE I

The following example illustrates the production of an anti-glaucoma drainage tube.

A well cleaned pericardium stroma was cut into 0.2 cm wide strips. The strips were frozen and thawed five times in a 0.9% solution of sodium chloride and distilled water (1:1). The strips were rinsed and placed into a solution of 1% ammonia and 1% ethyl alcohol (1:1) and incubated in the solution for a period of 48 hours. The ammonia/alcohol solution was drained and replaced with fresh solution. The strips were again incubated for 48 hours. The strips were then rinsed five times in distilled water, each rinse was carried out for a time period of 15 minutes. The pH of the waste solution was monitored and rinsing was completed when the pH reached 6.7 to 7.0. The strips were then packed in vials containing 70% ethyl alcohol and were sterilized with gamma irradiation. The strips were then formed into anti-glaucoma drainage tubes. After bacteriological tests, the tubes were sent to a clinic for use in patients.

EXAMPLE II

The following example illustrates the preparation of a scleroplastic material.

A well-cleaned pericardium stroma was cut into standard pieces. The pieces were frozen and thawed 5 times in a 0.9% solution of sodium chloride and distilled water (1:1). The pieces were then incubated in a solution of 1% ammonia and 1% ethyl alcohol (1:1). Incubation was conducted for a time period of 50 hours. The ammonia/alcohol solution was drained, replaced with fresh solution and the tissue was re-incubated for 50 hours. The pieces were then rinsed 5 times in distilled water for a period of 20 minutes for each rinse. Rinsing was complete as soon as pH of the waste rinse solution reached 6.5 to 7.0 and the waste solution ammonia reaction was negative. The pieces were packed in vials containing 70% ethyl alcohol and sterilized with gamma irradiation. After bacteriological tests, the pieces were sent to a clinic for use in patients.

EXAMPLE III

The following example illustrates the preparation of a material for treating macular dystrophies.

A cleaned pericardium stroma was cut into disks. The disks were frozen and thawed five times in a 0.9% solution of sodium chloride and distilled water (1:1). The discs were rinsed and placed into a solution of 1% ammonia and 1% ethyl alcohol (1:1) and incubated for a period of 72 hours. The disks were rinsed five times in distilled water, for time period of 30 minutes each rinse. The waste solution pH was monitored and rinsing was complete when the pH reached 6.7 to 7.0. The disks were packed in vials containing 70% ethyl alcohol and sterilized with gamma irradiation. After bacteriological tests, the disks were sent to a clinic for use.

Other modifications of the present invention will occur to those skilled in the art subsequent to a review of the present application. These modifications and equivalents thereof are intended to be included within the scope of the invention.

What is claimed:

1. A method of preparing a biological material suitable for use in ophthalmology, comprising the steps of:

providing animal pericardium;

subjecting said animal pericardium to multiple steps of freezing and thawing in a salt solution, said solution comprising a mixture of about 0.9% sodium chloride solution and distilled water in about 1:1 proportions of sodium chloride to distilled water; and incubating said animal pericardium in a solution of ammonia and ethyl alcohol to produce a biological material suitable for use in ophthalmology.

2. The method of claim 1, wherein said solution of ammonia comprises a mixture of 1% ammonia/water solution and 1% ethyl alcohol/water solution in about 1:1 proportions of ammonia solution to ethyl alcohol solution.

3. The method of claim 2, comprising twice incubating the animal pericardium in said solution over a period of 48 to 72 hours.

4. The method of claim 1, further comprising:

after said step of incubating, subjecting said animal pericardium to multiple rinsing steps.

5. The method of claim 4, wherein said step of subjecting comprises rinsing the animal pericardium 5 times for 15 to 30 minutes each time, in distilled water.

6. The method of claim 5, further comprising sterilizing said animal pericardium.

7. The method of claim 6, wherein said sterilizing comprises placing said pericardium in a solution of 70% ethyl alcohol and sterilizing with about 2.5 megarads of gamma irradiation.

8. The method of claim 1, further comprising:

prior to said step of subjecting, mechanically cleaning and cutting a raw material of animal origin to provide said animal pericardium.

9. The method of claim 1, further comprising:

after said incubating, forming said biological material into an anti-glaucoma drainage tube.

10. The method of claim 1, further comprising:

after said incubating, preparing a scleroplastic material from said biological material.

11. The method of claim 1, further comprising:

after said incubating, forming said biological material into a material for treating macular dystrophies.

12. A biological material for use in ophthalmology, comprising the product of the process of claim 1.

13. A biological material for use in ophthamology, comprising the product of the process of claim 2.

14. A biological material for use in ophthamology, comprising the product of the process of claim 3.

15. A biological material for use in ophthalmology, comprising the product of the process of claim 4.

16. A biological material for use in ophthalmology, comprising the product of the process of claim 5.

17. A biological material for use in ophthalmology, comprising the product of the process of claim 6.

18. A biological material for use in ophthalmology, comprising the product of the process of claim 7.

19. A biological material for use in ophthalmology, comprising the product of the process of claim 8.

20. A biological material for use in ophthalmology, comprising the product of the process of claim 9.

21. A biological material for use in ophthalmology, comprising the product of the process of claim 10.

22. A biological material for use in ophthalmology, comprising the product of the process of claim 11.

* * * * *